United States Patent
Levin et al.

(10) Patent No.: US 8,415,327 B2
(45) Date of Patent: Apr. 9, 2013

(54) METHODS OF AND COMPOSITIONS FOR REDUCING CELL DEATH

(75) Inventors: Leonard A. Levin, Madison, WI (US); Yun Luo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 256 days.

(21) Appl. No.: 12/710,215

(22) Filed: Feb. 22, 2010

(65) Prior Publication Data

US 2010/0256093 A1     Oct. 7, 2010

Related U.S. Application Data

(60) Provisional application No. 61/154,262, filed on Feb. 20, 2009.

(51) Int. Cl.
| | |
|---|---|
| *A61K 31/69* | (2006.01) |
| *C07C 69/612* | (2006.01) |
| *C07F 5/02* | (2006.01) |
| *A61P 43/00* | (2006.01) |
| *C12N 5/07* | (2010.01) |
| *C12N 5/071* | (2010.01) |

(52) U.S. Cl. .............. 514/64; 560/105; 564/8; 435/325; 435/366; 435/404

(58) Field of Classification Search .................... 514/64; 560/105; 564/8; 435/325, 366, 404
See application file for complete search history.

*Primary Examiner* — Jennifer M Kim
(74) *Attorney, Agent, or Firm* — Quarles & Brady LLP

(57) ABSTRACT

Methods and compositions involving a class of boron-protected phenylphosphine agents having increased cell permeability and having improved chemical stability for treating or for preventing cell death-related diseases or conditions in a human or a non-human animal.

12 Claims, 17 Drawing Sheets

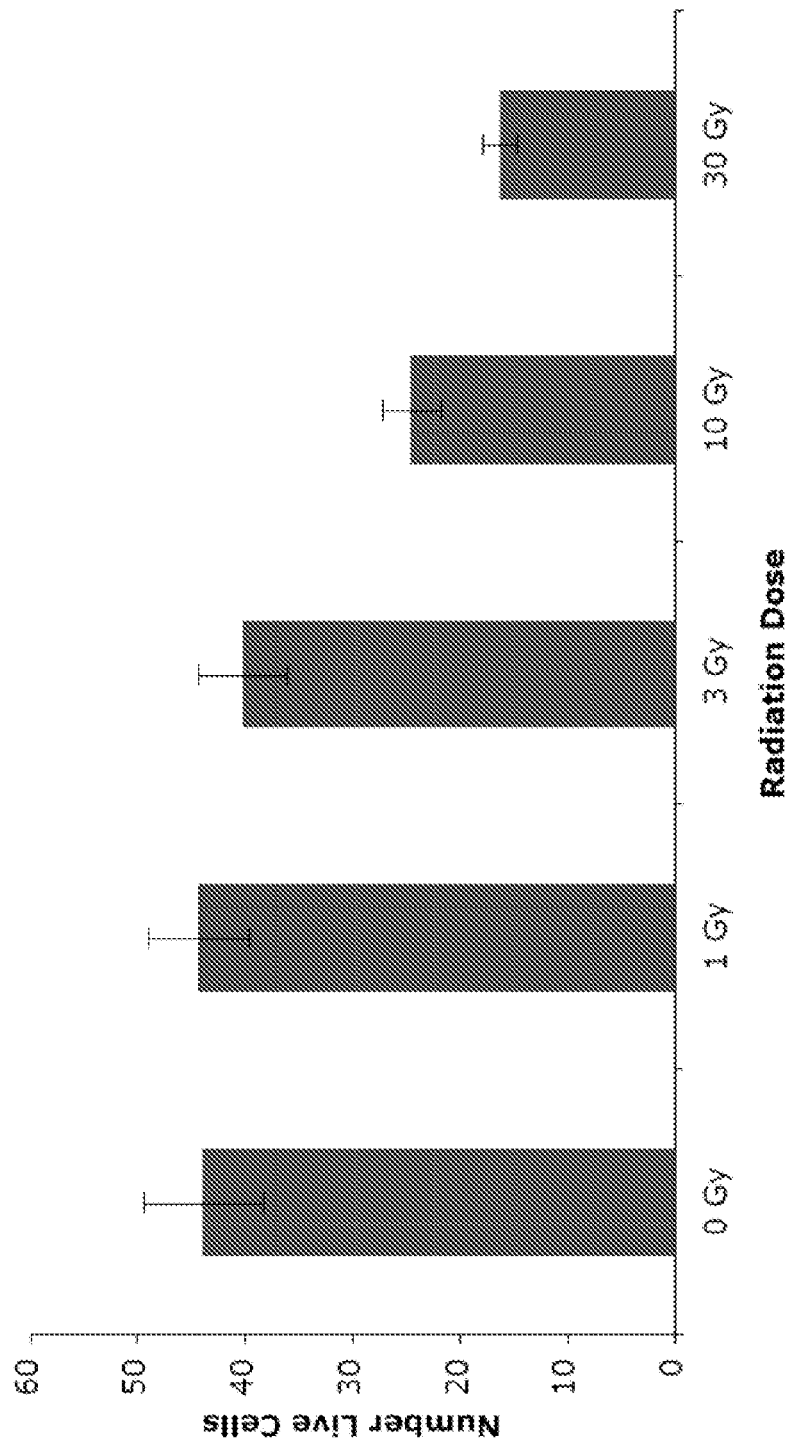

1 Gray Radiation, 72 hr Live Count

METHODS OF AND COMPOSITIONS FOR REDUCING CELL DEATH

CROSS-REFERENCE TO RELATED APPLICATIONS

This application claims the benefit of U.S. Provisional Patent Application No. 61/154,262, filed Feb. 20, 2009, incorporated herein by reference as if set forth in its entirety.

STATEMENT REGARDING FEDERALLY SPONSORED RESEARCH OR DEVELOPMENT

This invention was made with United States government support awarded by the following agency: NIH 1 R21 EY017970. The United States government has certain rights in this invention.

BACKGROUND

Cell death is a final pathway common to a variety of conditions and diseases including neurodegenerative disorders and opthalmological disorders, such as glaucoma, as well as in tissue injury caused by radiation. Although multiple mechanisms effectuate radiation damage, endothelial cell damage may be the primary mode of radiation injury (Fajardo and Berthrong, Pathol. Annu. 1:297 (1998); Reinhold and Buisman, Br. J. Radiol. 46:54 (1973); Reinhold and Buisman, Br. J. Radiol. 48:727 (1975); Paris et al., Science 293:293 (2001); Gaugler, Br. J. Radiol. Suppl. 27:100 (2005). Irradiated brain (Caveness, Natl. Cancer Inst. Monogr. 46:57 (1977)), lung (Ward et al., Radiat. Res. 136:15 (1993)), intestine (Hasleton et al., Histopathology 9:517 (1985)), and kidney (Keane et al., Am. J. Med. 60:127 (1976)) are characterized by decreased numbers or abnormal morphology of endothelial cells. Endothelial cells are by far the most actively dividing cells in neuronal tissue (Noetzel and Rox, Acta Neuropath. 3:326 (1964)), and endothelial cell apoptosis leads to disruption of the blood-brain barrier (Li et al., Cancer Res. 63:5950 (2003)), which is commonly observed in radiation injury (Young et al., Radiology 185:904 (1992)). Electron microscopic observations of irradiated brain demonstrate pinocytotic vesicles, infolded plasma membrane, and intracytoplasmic vacuoles, consistent with increased endothelial cell permeability (Llena et al., Arch. Pathol. Lab. Med. 100: 531 (1976)).

Large-scale population radiation exposure to a nuclear device or radiological dispersal device explosion would cause significant mortality and morbidity. Most available treatments of injury resulting from radiation are radioprotective in nature, i.e., treatments effective when administered before or around the time of exposure. However, effective radio-mitigation treatments, i.e., treatments effective when administered after exposure, remain to be elucidated. At present, radiomitigation is limited to off-label use of hematopoietic growth factors, iodide, and Prussian blue. Thus, there is a pressing need in the art for effective post-exposure treatment and, specifically, effective radiomitigants.

BRIEF SUMMARY

In one aspect, the present invention is summarized in that a method for protecting cells from cell death includes the step of exposing one or more cells to an effective amount of one or more compounds selected from the group consisting of bis (3-propionic acid hexyl ester)phenylphosphine borane complex (PB3), (3-propionic acid hexyl ester)diphenylphosphine borane complex (PB4), bis(3-propyl pivalamide)phenylphosphine borane complex (PB5), (2-ethyl acetamide)diphenylphosphine borane complex (PB6), bis(3-propionic acid octyl ester)phenylphosphine borane complex (PB7), and bis (3-propionic acid decyl ester)phenylphosphine borane complex (PB9).

In another aspect, the present invention is summarized in that a method for protecting cells from radiation damage includes the step of exposing one or more neuronal cells to an effective amount of one or more compounds having the formula:

(Formula I)

wherein $R_1$ to $R_3$ are identical or different and represent a carbon chain of one to thirty carbons, preferably one to twenty or one to ten carbons, and most preferably one to eight, two to seven, or three to six carbons; the carbon chain can be saturated, unsaturated, linear, branched, cyclic or polycyclic, and can have heteroatoms, such as F, Cl, Br, I, O, S, P and N, and preferably O, attached as part of the chain or of a side group.

The above compounds also include pharmaceutically acceptable salts thereof. Specifically excluded from the method of the present invention is the use of TCEP.

In some embodiments, at least one of $R_1$ to $R_3$ of Formula I is an aryl group (e.g. a phenyl group) or a substituted aryl group (e.g. a substituted phenyl group), at least one of $R_1$ to $R_3$ is an alkyl ester group (R—C(O)—O—R', either R or R' can be attached to P), or both. In other embodiments, the aromatic ring of the aryl or substituted aryl group is directly linked to the phosphorus.

In preferred embodiments, the lone pair of electrons on the phosphorus of Formula I is protected by a removable protective group $R_4$ (Formula II) such as H or $BH_3$. In more preferred embodiments, the lone pair of electrons is protected by $BH_3$.

(Formula II)

In other embodiments, $R_1$ to $R_3$ of Formula I are selected from an aryl group (e.g., a phenyl group), a substituted aryl group (e.g., a substituted phenyl group) and an alkyl ester group, wherein at least one of $R_1$ to $R_3$ is an aryl or substituted aryl group and at least one of $R_1$ to $R_3$ is an alkyl ester group. In preferred embodiments, the lone pair of electrons is protected by $BH_3$. In more preferred embodiments, the compounds defined by Formula I are bis(3-propionic acid methyl ester)phenylphosphine borane complex (PB1) and (3-propionic acid methyl ester)diphenylphosphine borane complex (PB2), described in detail below. Other preferred compounds are bis(3-propionic acid hexyl ester)phenylphosphine borane complex (PB3), (3-propionic acid hexyl ester)diphenylphosphine borane complex (PB4), bis(3-propyl pivalamide)phenylphosphine borane complex (PB5), (2-ethyl acetamide)diphenylphosphine borane complex (PB6), bis(3-propionic acid octyl ester)phenylphosphine borane complex (PB7), and bis(3-propionic acid decyl ester)phenylphosphine borane complex (PB9).

In some embodiments, the method of the present invention is employed to protect neuronal cells of a mammalian species.

In some embodiments, the method of the present invention is employed to protect endothelial cells of a mammalian species.

In some embodiments, the one or more cells are exposed to an effective amount of one or more compounds after exposure to radiation.

In some embodiments, the method of the present invention is employed to alleviate or prevent tissue and cell damage caused by radiation in a mammal. Specifically, the invention involves administering to a mammal small molecules that are effective radio-protectants and/or radio-mitigants prior to, during, or after exposure to radiation.

In a second aspect, the PB3, PB4, PB5, PB6, PB7, PB9 compounds and pharmaceutical compositions comprising one of the compounds and a pharmaceutically acceptable carrier are also within the scope of the present invention.

The previously described embodiments of the present invention have many advantages, including a first advantage that the compounds protect cells in vitro as well as in vivo.

It is a second advantage that the methods and compounds are useful in enhancing survival and viability of tissue used in transplants.

It is a third advantage that the compounds may be applied topically.

It is a fourth advantage that the compounds possess antioxidant properties and may therefore be used to protect against or mitigate oxidative damage.

It is a fifth advantage that the compounds can be administered before, during, or after exposure to radiation.

These and other features, aspects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the appended claims for interpreting the scope of the invention

BRIEF DESCRIPTION OF THE DRAWINGS

The invention will be better understood and features, aspects, and advantages other than those set forth above will become apparent when consideration is given to the following detailed description thereof. Such detailed description makes reference to the following drawings, wherein:

FIGS. 4A-L show irradiated murine retinal endothelial cell survival. The endothelial cells were exposed to 100 pM, 1 nM, 10 nM, or 100 nM PB1 either 18 hrs before, immediately before, or after irradiation. Cell viability was assessed after 48 hrs (FIG. 4A-F) or 72 hrs (FIG. 4G-L).

Figure 1A:
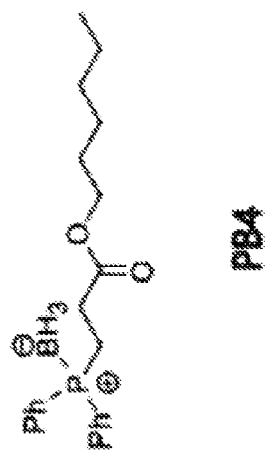
FIG. 1A-F show the chemical structures of PB3, PB4, PB5, PB6, PB7, and PB9, respectively. PB3 (FIG. 1A) and PB4 (FIG. 1B) have two and one hexyl ester side chains, respectively, and are designed to cross the blood brain barrier better than PB1 and PB2, in which the side chains are methyl esters. PB5 (FIG. 1F) has two pivalamide side chains and is designed to both have increased corneal permeability and increased concentration within negatively charged mitochondria. PB6 (FIG. 1C) and PB5 have two and one methyl amide side chains, respectively, and are designed to enter mitochondria better than PB1 and PB2, in which the side chains are methyl esters. PB7 (FIG. 1D) has two octyl ester side chains and is designed to enter cells, cross the blood-brain barrier, or cross the blood-retinal bather better than PB1, in which the side chains are methyl esters. PB9 (FIG. 1E) has two decyl ester side chains and is designed to cross into cells or cross the blood-brain barrier or cross the blood-retinal barrier better than PB1, in which the side chains are methyl esters.
Figure 1B:
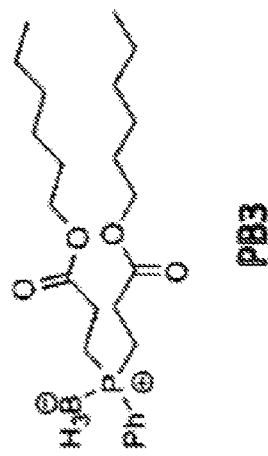
Figure 1C:
Figure 1D:
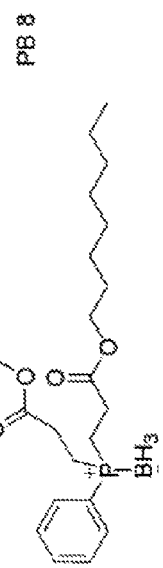
Figure 1E:
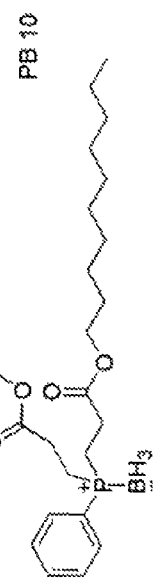
Figure 1F:
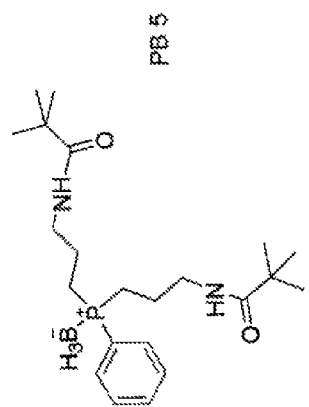

The present invention is not intended to be limited to any particular operative theory; alternative or additional mechanisms of action, such as reducing other thiol modifications and reducing other molecules, are certainly possible.

DESCRIPTION OF PREFERRED EMBODIMENTS

Unless defined otherwise, all technical and scientific terms used herein have the same meaning as commonly understood by one of ordinary skill in the art to which the invention belongs. Although any methods and materials similar to or equivalent to those described herein can be used in the practice or in the testing of the present invention, the preferred methods and materials are now described.

As used herein, the term "neuronal cells" encompasses any differentiated neuronal cells such as neurons (e.g. RGCs) or glial cells (e.g., astrocytes and oligodendrocytes) of either the central or the peripheral nervous system. The term also encompasses neuronal stem cells and neuronal progenitor cells. Neuronal cells encompassed by the term can assume any form such as the form of a tissue or dissociated neuronal cells (e.g. in a cell suspension).

As used herein, the term "cell death" encompasses apoptosis, necrosis and other types of cell death, such as mixed type of cell death.

As used herein, an "effective amount" of one or more compounds means an amount effective to protect cells from cell death. For the purpose of the present invention, the protective effect of a compound can be measured, for example; by a longer cell survival time, a decrease in the percentage of cells that die within a particular period of time or both in compound-treated cells in comparison to control cells. Of course, what constitutes the effective amount will depend on a variety of factors, including, for example, the size, the age and the condition of the individual, as well as on the mode of delivery. It is well within the ability of one of ordinary skill in the art to determine the effective amount.

The compounds of the present invention can protect cells and tissue both in vitro (e.g. in cell culture) and in vivo (e.g. in a human or in a non-human animal). For example, protective compounds may be used with cultured cells or with tissue maintained ex vivo for purposes of transplantation into one or more sites in the eye of a patient suffering from an optic neuropathy. In this instance, the protective compound would enhance survival and viability of the tissue and increase the chances of a successful graft. Use of protective compounds in this context can be achieved with any of the available culturing or grafting procedures.

For in vivo applications, the compounds of the present invention are used to treat a subject (e.g., a patient) who is experiencing a cell death-related disease or condition. The compounds can also be used to prevent the disease or the condition (including partial prevention such as delay and minimizing symptoms at onset of disease or condition) in an at-risk individual not yet showing signs of the disease or the condition. In these applications, one or more compounds of the present invention are administered to a subject in an effective amount to treat or to prevent the disease or the condition.

Examples of cell death-related diseases or conditions that can be treated or can be prevented include, but are not limited to various neurodegenerative disorders (e.g. Alzheimer's disease, Huntington's Disease, prion diseases, Parkinson's Disease, amyotrophic lateral sclerosis, ataxia telangiectasia, spinobulbar atrophy, age-related reduction in number or in function, macular degeneration, retinal degeneration, dominant optic atrophy and Leber's hereditary optic neuropathy), diseases and conditions induced under various conditions of ischemia and/or excitotoxicity (e.g. ischemic stroke, hemorrhagic stroke, retinal ischemia, diabetic retinopathy, and ischemic optic neuropathy), diseases due to nervous system trauma (e.g. spinal cord injury or traumatic optic neuropathy), diseases due to inflammation (e.g. optic neuritis or multiple sclerosis), diseases due to infection (e.g. meningitis and toxoplasmosis optic neuropathy), diseases and conditions induced by certain medications or irrigating solutions (e.g. optic neuropathy induced by ethambutol or methanol), diseases due to other etiologies (e.g. glaucoma), and diseases and conditions associated with exposure to radiation.

The compounds can be provided in a pharmaceutically acceptable carrier and can be administered to a subject via a topical or a systemic route, such as those described below.

In an exemplary embodiment, the compounds of the present invention are used to treat or to prevent a disorder related to neuronal cell death, including, but not limited to, glaucomatous optic neuropathy, ischemic optic neuropathy, inflammatory optic neuropathy, compressive optic neuropathy and traumatic optic neuropathy. In a preferred embodiment, the compounds of the present invention are used to treat or to prevent glaucoma.

It is reasonable to expect that the more neuronal cells that a protective compound contacts, the more pronounced its protective effect. Preferably, the method of the present invention allows a protective compound to contact at least about 25%, 50% or even as many as 95% or 100% of the cells.

Preferably, contacting the neuronal cells with one or more compounds of the present invention will reduce cell death by at least about 50% when compared to untreated cells. However, it is expected that a reduction of cell death of 25%, 10% or 5% will extend the vision of the treated subject. In a human subject, a reduction in cell death may be estimated by extrapolation from functional and structural assays.

Functional assays involve evaluating changes in visual function over time, specifically, visual acuity and visual fields. It is reasonably expected that a reduction in the rate of neuronal cell death following initiation of treatment may be correlated with a reduction in the rate of loss of visual function over time. Structural assays involve visualizing or measuring the optic nerve head or the retinal nerve fiber layer with an opthalmoscope or other device to assess optic disc atrophy, disc cupping or loss of nerve fibers.

A protective compound can be made to target specific cells, such as a neuronal cell, by linking it to an antibody or other molecule that can bind a cell surface antigen, such as Thy-1, which is a major retional ganglion cell surface protein. For example, a protective compound can be covalently linked to a cell-specific aptamer. The Systematic Evolution of Ligands by EXponential enrichment (SELEX) procedure can be used to produce RNA molecules that bind to Thy-1. See Tuerk C & Gold L, Science 249:505-510 (1990), incorporated herein by reference as if set forth in its entirety. A library of RNA molecules can be generated by in vitro transcription from a commercially generated DNA library of sequences having a combinatorially rich random nucleotides core flanked by primer binding sequences (e.g., FFFFFFFFFFFFFFFF RRRRRRRRRRRRRRRR, wherein FFFFFFFFFFFFFFFF represents a binding site for a forward primer, wherein RRRRRRRRRRRRRRRR represents a binding site for a reverse primer, and wherein is twenty-four to thirty-six combinatorially rich random nucleotides). Purified Thy-1 can then be attached to sepharose beads, the RNA molecules allowed to bind, the beads washed, and the bound RNA eluted. The eluted RNAs are molecules with increased affinity for Thy-1. They can then be reverse transcribed and amplified in a PCR reaction (using the forward and the reverse primers that bind to all of the molecules). The amplimers will then be transcribed, and the process repeated. The optimal RNA sequences are then synthesized with resistant nucleotides and covalently attached to a protective compound.

For treating a cell death-related disorder, protective compounds may be administered singly or in combinations of two or more protective compounds, with or without other active drugs, including without limitation, ocular hypotensive and other anti-glaucoma agents (e.g. prostaglandins or prostanoids, carbonic anhydrase inhibitors, beta-adrenergic agonists and antagonists, alpha-adrenergic agonists, N-acetyl cysteine, glutathione or other anti-glaucoma agents) known to those skilled in the art. Protective compounds may be delivered within any appropriate pharmaceutical formulation by topically (e.g. eye drops), transsclerally, intravitreally, intraorbitally (e.g. retrobulbar or peribulbar injection), subconjunctivally, orally, intravenously, subcutaneously, intramuscularly, intraocularly, transdermally, bucally, intravaginally, rectally, nasally, intracerebrally, intraspinally or any of a variety of novel alternative drug delivery systems including those currently marketed, or any other means that is appropriate to the compound(s) in question.

For easy access to neuronal cells, protective compounds can be delivered through injection or depot injection in or around the vitreous, the retinal nerve fiber layer, the optic nerve fibers or the targets of neuronal cells within the brain. Topical ophthalmic compositions are employed when the compounds are to be dosed topically. Preferably, the topically dosed compounds are formulated for sustained release over a period of time. See Remington's Pharmaceutical Sciences (14th Ed. 1970); Joshi J, Ocul. Pharmacol. 10:29-45 (1994); McCalden et al., Experientia 46:713-715 (1990); Feist et al., J. Cataract Refract. Surg. 21:191-195 (1995); Cheng et al., Invest. Opthalmol. Vis. Sci. 36:442-453 (1995); and Chetoni et al., J. Ocul. Pharmacol. Ther. 129:245-252 (1996), each of which is incorporated herein by reference as if set forth in its entirety. Also preferably, the topically dosed compounds are formulated to increase penetration and to increase corneal contact time. See Meseguer et al., J. Ocular. Pharm. Ther. 12:481-488 (1996); and Nelson et al., J. Am. Optom. Assoc. 67:659-663 (1996), each of which is incorporated herein by reference as if set forth in its entirety.

The preparation of topical compositions is well known in the art. Generally, topical ophthalmic compositions useful in the present invention are in the form of a solution, a suspension, a gel or formulated as part of a device, such as a collagen shield or other bioerodible or non-bioerodible device.

Various excipients may be contained in the topical solutions, suspensions, or gels of the present invention. For example, buffers (e.g. borate, carbonate and phosphate), tonicity agents (e.g. sodium chloride, potassium chloride and polyols), preservatives (e.g. polyquatemiums, polybiguanides and BAS), chelating agents (e.g. EDTA), viscosity enhancing agents (e.g. polyethoxylated glycols) and solubility agents (e.g. polyethoxylated castor oils, including polyoxl-35 castor oil, Polysorbate 20, 60 and 80; Pluronic® F-68, F-84 and P-103; or cyclodextrin) may be included in the topical compositions.

Likewise, a variety of gels may be useful in topical gel compositions of the present invention, including, but not limited to, carbomers, polyvinyl alcohol-borate complexes, xanthan, gellan or guar gums.

Topical bioerodible and non-bioerodible devices (e.g. conjunctival implant) may be used for topical administration of protective compounds. See Weiner A, "Polymeric Drug Delivery Systems For the Eye," in Polymeric Site-Specific Pharmacotherapy, (A. J. Domb, Ed., John Wiley & Sons, pp. 316-327, 1994). Topical administration is suitable for facilitating the delivery of the protective compounds described herein to enable chronic treatment of a particular tissue.

Protective compounds may also be delivered on a solid or a semisolid scaffold. For example, for treatment of the eye, delivery is accomplished by placing the support in a region of the eye selected from the group consisting of an eyelid, a conjunctiva, a sclera, a vitreous, a retina, an optic nerve sheath, an intraocular location and an intraorbital location. Additionally, protective compounds may be delivered slowly over time to the eye through the use of contact lenses. This regimen is generally performed by first soaking the lenses in a protective compound and then applying the contact lenses to the eye.

When the protective compounds are administered during surgical procedures, such as through injection or perfusion, the use of irrigating solutions as vehicles are most preferred. The most basic irrigating solutions generally comprise sterile saline or phosphate-buffered saline (PBS). More advanced irrigating solutions, however, are preferred. Also contemplated are sustained-release formulations. Specifically contemplated is the administration of the protective compounds during intraocular, intracerebral, or intraspinal surgical procedures via, for example, retrobulbar or periocular injection (Ophthalmic Surgery: Principles of Practice, W. B. Sanders Co., Philadelphia, Pa., USA, pp. 85-87 (G. L. Spaeth, Ed., 1990)), intraocular perfusion or injection, or intraspinal or intracerebral injection or perfusion.

As used herein, the term "physiologically balanced irrigating solution" refers to a solution adapted to maintain the physical structure and the function of tissues during invasive or noninvasive medical procedures. This type of solution typically contains electrolytes, such as sodium, potassium, calcium, magnesium and/or chloride; an energy source, such as dextrose; and a bicarbonate buffer to maintain the pH of the solution at or near physiological levels. Various solutions of this type are known (e.g. Lactated Ringers Solution, BSS, RTM, BSS Plus RTM, Sterile Irrigating Solution and Sterile Intraocular Irrigating Solution).

Pharmaceutical compositions of the protective compounds can be formulated for systemic use using techniques well known in the art. Orally administered compositions are generally in the form of tablets, hard or soft gelatin capsules, suspension, granules, powders or other typical compositions and contain excipients typically present in such compositions. Methods for the preparation of such oral vehicles are well known by those skilled in the art. Parenterally administered compositions are generally in the form of injectable solutions or suspensions. Methods for the preparation of such parenteral compositions are well-known by those skilled in the art.

It is appreciated that the compounds of the present invention are good electron donors (upon removal of the removable protective group if present), and thus have antioxidant activities. Accordingly, these compounds can be used to protect against oxidative damage to human or animal cells, tissues and organs in general. The role of reactive oxygen species (ROS) in the etiology of human diseases (e.g. cancer, atherosclerosis, rheumatoid arthritis, inflammatory bowel diseases, immune system dysfunctions, brain function decline and connective tissue dysfunction) and conditions (e.g. radiation damage) is well-established.

Diseases and conditions caused by oxidative damage can be prevented or can be treated with the compounds of the present invention. The specifics on using these compounds for this purpose, such as the appropriate dosage and the route of administration, can be readily determined by a skilled artisan as described above in the context of protecting cells from cell death-related diseases and conditions.

The invention will be more fully understood upon consideration of the following non-limiting examples.

EXAMPLES

Example 1

Preventing RGC Menadione-Induced Cell Death In Vitro

Experimental Procedures

Synthesis of PB3, PB4, PB5, PB6, PB7, PB9: Borane-protected phosphines PB3, PB4, PB5, PB6, PB7, and PB9 (FIG. 1A-F) were designed for improved cell permeability and mitochondrial targeting. The long alkyl groups on PB3 and PB4 increase lipophilicity and thereby enhance the ability of PB3 and PB4 to cross cellular memberanes. PB3 and PB4 also have an enhanced ability to cross the blood brain barrier compared to related compounds. PB5 has two pivalamide side chains and has an increased corneal permeability and increased concentration within negatively charged mitochondria. PB6 becomes positively charged by intracellular amidase cleavage, which facilitates entry of PB6 into the negatively charged mitochondrion. PB7 has two octyl ester side chains and PB9 has two decyl ester side chains. Both PB7 and PB9 enter into cells, cross the blood-brain barrier, or cross the blood-retinal barrier better than PB1.

Synthesis of bis(3-propionic acid hexyl ester)phenylphosphine borane complex (PB3)

Phenylphosphine (2.0 g, 18 mmol) was dissolved in acetonitrile (2 ml, degassed) in a flame-dried round bottom flask under Ar(g). Hexyl acrylate (6.34 ml, 36 mmol) was added at 0° C. After complete addition of hexyl acrylate, the reaction was stirred at room temperature for 3 days. The solvent was removed en vacuo. The residue was dissolved in dry THF under an argon atmosphere. This solution was cooled to 0° C. and borane-THF (1.0 M in THF, 18 ml, 18 mmol) was added slowly. The solvent was removed under reduced pressure, and the residue was purified by flash chromatography (silica gel, 50% v/v ethyl acetate in hexanes). Phosphine-borane complex 3 (PB3) was isolated as a clear oil (1.6 g, 3.66 mmol, 20.4% yield).

Spectral data: $^1$H NMR (300 MHz, CDCl$_3$) δ7.78-7.70 (m, 2H), 7.57-7.47 (m, 3H), 4.00 (t, 4H), 2.70-2.56 (m, 2 µl), 2.41-2.19 (m, 6H), 1.65 (m, 4H), 1.38 (m, 8H), 0.86 (t, 6H), 1.40-0.40 (m, 3H) ppm. MS (ESI) m/z 459.2827 (MNa$^+$ [C$_{24}$H$_{42}$OBO$_4$PNa$^+$]=459.2827).

Synthesis of (3-propionic acid hexyl ester)diphenylphosphine borane complex (PB4)

Borane-diphenylphosphine complex (0.190 g, 1.0 mmol) was dissolved in acetonitrile (8 ml) in a flame-dried round bottom flask under Ar(g) at room temperature. Hexyl acrylate (0.212 ml, 1.2 mmol) was added to this mixture. The reaction mixture was allowed to stir at room temperature for 3 days. The acetonile was removed en vacuo, and the residue was purified by flash chromatography (silica gel, 80% v/v ethyl acetate in hexanes). Phosphine-borane complex 4 (PB4) was isolated as a pale yellow oil (0.119 g, 0.334 mmol, 33.4% yield).

Spectral data: $^1$H NMR (300 MHz, CDCl$_3$) δ7.72-7.65 (m, 5H), 7.51-7.45 (m, 6H), 4.05 (t, 2H), 2.55 (m, 4H), 1.55 (m, 2H), 1.38 (m, 6H), 0.86 (t, 3H), 1.4-0.4 (m, 3H) ppm; MS (ESI) m/z 373.2452 (MNa$^+$[C$_{21}$H$_{30}$BO$_2$PNa$^+$]=373.2452).

Synthesis of (2-Ethyl acetamide)diphenylphosphine borane complex (PB6)

2-(Diphenylphosphino)ethylamine (0.2 g, 0.87 mmol) was dissolved in a mixture of 20 mL of acetic anhydride and 5 mL pyridine under Ar (g). The reaction mixture was stirred at room temperature for 3 days. The solvents were removed en vacuo. The residue was dissolved in ethyl acetate and washed with 0.5 M HCl, water, and brine. The organic layers were dried over MgSO$_4$(s), filtered, and concentrated en vacuo. The residue was purified by flash chromatography (silica gel, 80% v/v ethyl acetate in hexanes). Phosphine 6 was isolate as a white solid. $^1$H NMR (300 MHz, CDCl$_3$) δ 7.51-7.45 (m, 10H), 5.72 (s, 1H), 3.45 (m, 2H), 2.25 (m, 2H), 1.88 (s, 3H), 0.86 (t, 3H) ppm. Phosphine 6 was dissolved in dry THF under an argon atmosphere. This solution was cooled to 0° C. and borane-THF (1.0 M in THF, 1 ml, 1 mmol) was added slowly. The reaction was stirred at 0° C. for 45 min and then at room temperature for an additional 3 h. The solvent was removed under reduced pressure, and the residue was purified by flash chromatography (silica gel, 80% v/v ethyl acetate in hexanes). Phosphine-borane complex 6 (PB6) was isolated as a white solid (0.16 g, 0.59 mmol, 67.8% yield).

Spectral data: $^1$H NMR (300 MHz, CDCl$_3$) ☐ 7.72-7.65 (m, 4H), 7.51-7.45 (m, 6H), 5.95 (s, 1), 3.55 (m, 2H), 2.55 (m, 2H), 1.85 (s, 3H), 2.0-1.0 (m, 3H) ppm; MS (ESI) m/z 308.3 (MN$^+$[C$_{16}$H$_{21}$BNOPNa$^+$]=308.3).

Synthesis of bis(3-propyl pivalamide)phenylphosphine borane complex (PB5)

After the dried THF was aerated by Argon gas for 10 min, 6.9 g (50 mmoL) of K$_2$CO$_3$ was added. After the mixture was aerated 2 Minutes by Argon gas, 2 g of bis(3-aminopropyl)-phenylphosphine and 4 mL of pivaloyl chloride were added into the mixture separately at 0° C. The ice bath was removed after addition. After the reaction mixture was stirred for 0.5 hour, it was heated to 60° C., and it was kept at 60° C. for 10 hours under Argon gas. After the reaction mixture was cooled down to 0° C., 35 mL of 1M BH$_3$.THF was added. After the reaction was stirred under Argon gas overnight, it was purified by chromatography to obtain 0.5 g of bis(3-propyl pivalamide)phenylphosphine borane complex (PB5).

Spectral data: $^1$H NMR (300 MHz, CDCl$_3$) δ 7.72-7.65 (m, 2H), 7.51-7.45 (m, 3H), 5.95 (s, 2H), 3.25 (m, 4H), 1.5-2.0 (m, 8H), 1.15 (18S), 1.0-0 (m, 3H) ppm; MS (ESI) m/z 428.3 (MNa$^+$[C$_{22}$H$_{40}$BN$_2$O$_2$PNa$^+$]=308.3).

Synthesis of bis(3-propionic acid octyl ester)phenylphosphine borane complex (PB7)

Bis(3-propionic acid methyl ester)phenylphosphine borane complex (PB1) (0.5 g) was dissolved in 10 mL of octanol, and 0.5 g of PTSA was added. The reaction mixture was stirred under Argon gas at 60° C. for 4 hours. After removal of octanol, it was purified by chromatograph (EtOAc/hexane=2/8) to get 0.45 g of bis(3-propionic acid octyl ester)phenylphosphine borane complex (PB7) as colorless liquid.

Spectral data: $^1$H NMR (300 MHz, CDCl$_3$) δ7.78-7.70 (m, 2H), 7.57-7.47 (m, 3H), 4.05 (t, 4H), 2.70-2.56 (m, 2H), 2.41-2.19 (m, 6H), 1.65 (m, 4H), 1.38 (m, 20H), 0.86 (t, 6H), 1.40-0.40 (m, 3H) ppm. MS (ESI) m/z 510.3993 (MNa$^+$ [C$_{28}$H$_{50}$OBO$_4$PNH$_4$$^+$]=510.3993).

Synthesis of bis(3-propionic acid decyl ester)phenylphosphine borane complex (PB9)

Bis(3-propionic acid methyl ester)phenylphosphine borane complex (PB1) (2.5 g) was dissolved in 10 mL of decanol, and 0.5 g of PTSA was added. The reaction mixture was stirred under Ar gas at 60° C. for 12 hours. After removal of decanol, it was purified by chromatography (EtOAc/hexane=2/8) to get 2.00 g of bis(3-propionic acid decyl ester) phenylphosphine borane complex (PB9) as colorless liquid.

Spectral data: $^1$H NMR (300 MHz, CDCl$_3$) δ7.78-7.70 (m, 2H), 7.57-7.47 (m, 3H), 4.05 (t, 4H), 2.70-2.56 (m, 2H), 2.41-2.19 (m, 6H), 1.65 (m, 4H), 1.38 (m, 28H), 0.86 (t, 6H), 1.40-0.40 (m, 3H) ppm. MS (ESI) m/z 565.4541 (MNa$^+$ [C$_{32}$H$_{58}$OBO$_4$PNH$_4$$^+$]=565.4541).

Cell Culture: Cells of RGC-5 (ATCC Deposit Accession No. PTA-6600), a neuronal cell line, were suspended in growth medium and plated in 96-well plates at a density of 2,000 cells per well. After 24 hours in culture, cells were treated with 17.8 µM menadione (Sigma-Aldrich, St. Louis, Mo.). Menadione creates oxidative stress resulting in cell death. PB3, PB4, or PB6 was added to the wells directly before menadione treatment. After 24 hours of menadione treatment, the cells were stained with calcein-AM and photographed. Calcein-AM-positive (i.e., viable) cells were counted using NIH ImageJ software (National Institutes of Health, available online) to determine whether any of the added compounds protected RGC-5 cells from menadione-induced cell death.

Results

The borane-protected phosphines PB3, PB4, and PB6 were neuroprotective against menadione-induced cell death in RGC-5 cells. PB3 significantly protected RGC-5 cells from menadione-induced cell death at concentrations of 100 µM (30.9±4.3% of the cells were protected (p=0.000032)), 1 µM (46.4±16.8% of the cells were protected (p=0.024)), and 10 µM (38.3±12.2% of the cells were protected (p=0.014)). PB4 and PB6 were less effective neuroprotectants than PB3. PB4 was most effective at a concentration of 1 µM resulting in protection of 19.0±5.5% (p=0.031) of the cells. PB6 was most effective at a concentration of 10 pM resulting in protection of 25.6±8.4% of the cells (p=0.016). Differences in the effectiveness of these phosphines may be due to differences in cell permeability or intracellular targeting.

Example 2

Preventing Antimycine A-Induced Cell Death In Vitro

Experimental Procedures

Synthesis of PB1 and PB2: Chemicals and solvents were from Aldrich Chemical (Milwaukee, Wis.). Reactions were monitored by thin-layer chromatography and were visualized by ultraviolet light or staining with $I_2$. NMR spectra were obtained with a Bruker AC-300 or Varian Inova-600 spectrometer. Phosphorus-31 NMR spectra were proton-decoupled and referenced against an external standard of deuterated phosphoric acid. Mass spectra were obtained with electrospray ionization (ESI) or matrix-assisted laser desorption/ionization (MALDI) techniques.

Figure 2:
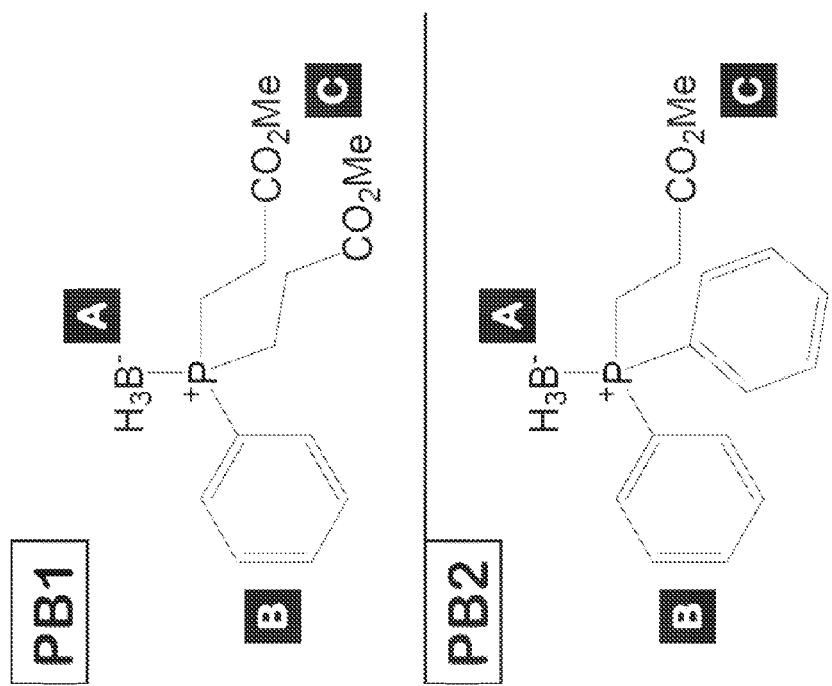
FIG. 2 shows the structure of PB1 and PB2. A borane protects the phosphine from oxidation, and thus stabilizes the molecule (A). The phenyl group is nonpolar (which is likely to increase the molecule's cell permeability), delocalizes the electron pair of the phosphino group by resonance and provides minimal steric hindrance (B). The methyl esters are likely cleaved by cytosolic esterases, resulting in an anionic molecule that is unlikely to exit the cytosol (C).

Synthesis of bis(3-propionic acid methyl ester)phenylphosphine borane complex (PB1) (FIG. 2)

Phosphine 1: See Rampal et al., J. Am. Chem. Soc. 103: 2032-2036 (1981), incorporated herein by reference as if set forth in its entirety. Phenylphosphine (10 g, 90 mmol) was dissolved in acetonitrile (10 ml, degassed) in a flame-dried, round bottom flask under Ar(g). Potassium hydroxide (1.0 N, 1.0 ml) was added to this mixture, and the resulting solution was cooled to 0° C. Methyl acrylate (16.2 ml, 180 mmol) was added at a rate that maintained the reaction temperature below 35° C. Upon complete addition of methyl acrylate, the reaction was heated at 50° C. for 8 hours. The reaction mixture was then washed with brine (2×10 ml). The organic layer was dried over $MgSO_4$(s), filtered, and concentrated en vacuo. The residue was purified by distillation with the desired product distilling at 160-170° C. (0.5 mm Hg). Phosphine 1 was isolated as a clear liquid (20.7 g, 73 mmol, 81% yield).

Spectral data: $^1$H NMR (300 MHz, $CDCl_3:CD_3OD$) δ 7.54-7.48 (m, 2H), 7.37-7.30 (m, 3H), 3.62 (s, 6H), 2.46-2.23 (m, 4H), 2.10-2.03 (m, 4H) ppm; $^{13}$C NMR (75 MHz, THF-$d_6$) δ 173.25 (d, J=12.9 Hz), 133.51 (d, J=15.5 Hz), 132.28 (d, J=19.4 Hz), 129.22, 128.43 (d, J=7.2 Hz), 51.47, 30.22 (d, J=16.9 Hz), 22.63 (d, J=11.9 Hz) ppm; $^{31}$P NMR (121 MHz, $CDCl_3:CD_3OD$) δ −23.06 ppm; MS (ESI) m/z 305.0905 (MNa$^+$[$C_{14}H_{19}O_4PNa^+$]=305.0919).

PB1: Phosphine 1 (20.7 g, 73 mmol) was dissolved in dry tetrahydrofuran (THF) in a flame-dried round bottom flask under Ar(g). This solution was cooled to 0° C. and borane-THF (1.0 M in THF, 80.6 ml, 80.6 mmol) was added slowly. The reaction was stirred at 0° C. for 45 minutes and then was stirred at room temperature for an additional 1.5 hours. The solvent was removed under reduced pressure, and the residue was purified by flash chromatography (silica gel, 80% v/v methylene chloride in hexanes). PB1 was isolated as a clear oil (7.6 g, 25.6 mmol, 35% yield).

Spectral data: $^1$H NMR (300 MHz, $CDCl_3:CD_3OD$) δ 7.78-7.70 (m, 2H), 7.57-7.47 (m, 3H), 3.64 (s, 6H), 2.70-2.56 (m, 2H), 2.41-2.19 (m, 6H), 0.68 (m, 3H) ppm; $^{13}$C NMR (75 MHz, THF-$d_6$) δ 172.29 (d, J=19.1 Hz), 131.88 (d, J=13.5 Hz), 131.84, 128.93 (d, J=12.3 Hz), 126.11 (d, J=61.4 Hz), 51.83, 27.37, 20.71 (d, J=45.4 Hz) ppm; $^{31}$P NMR (121 MHz, $CDCl_3:CD_3OD$) δ 17.34 (d, J=70.4 Hz) ppm; MS (ESI) m/z 318.1292 (MNa$^+$ [$C_{14}H_{22}BO_4PNa^+$]=318.1283).

Synthesis of (3-propionic acid methyl ester)diphenylphosphine borane complex (PB2) (FIG. 2)

PB2: See Imamoto et al., J. Am. Chem. Soc. 107:5301-5303 (1985), incorporated herein by reference as if set forth in its entirety. Borane-diphenylphosphine complex (0.190 g, 1.0 mmol) was dissolved in methanol (8 ml) in a flame-dried, round bottom flask under Ar(g) at room temperature. Potassium hydroxide (0.0028 g, 0.05 mmol) was added to this mixture, followed by the drop-wise addition of methyl acrylate (0.108 ml, 1.2 mmol). The reaction mixture was allowed to stir at room temperature for 6 hours, after which the methanol was removed en vacuo. The residue was taken up in dichloromethane (10 ml) and was washed with 0.5 N HCl (1×5 ml) and brine (1×5 ml). The aqueous layers were washed with dichloromethane (10 ml), and the combined organic layers were dried over $MgSO_4$(s), filtered and concentrated en vacuo. The residue was purified by flash chromatography (silica gel, 30% v/v ethyl acetate in hexanes). PB2 was isolated as a pale yellow oil (0.219 g, 0.76 mmol, 76% yield).

Spectral data: $^1$H NMR (300 MHz, $CDCl_3$) δ 7.72-7.65 (m, 5H), 7.51-7.45 (m, 5H), 3.64 (s, 3H), 2.55 (m, 4H), 0.96 (m, 3H) ppm; $^{13}$C NMR (75 MHz, $CDCl_3$) δ 132.37 (d, J=9.20 Hz), 131.67, 129.17 (d, J=10.1 Hz), 128.84, 52.24, 28.01, 21.15 (d, J=39.5 Hz) ppm; $^{31}$P NMR (121 MHz, $CDCl_3$) δ 16.26 (d, J=59.0 Hz); MS (ESI) m/z 309.1190 (MNa$^+$ [$C_{16}H_{20}BO_2PNa^+$]=309.1192).

Cell Culture: RGC-5 cells were cultured in Dulbecco's modified Eagle's medium (DMEM) (Mediatech, Inc., Manassas, Va.). containing 1 g/L glucose, supplemented with 10% fetal bovine serum, 100 U/mL penicillin, and 100 µg/mL streptomycin (Mediatech, Inc.). Cells were passaged every 48 to 72 hours when cells were approximately 60 to 75% confluent, replated at a 1:20 dilution in a 75 cm$^2$ flask in 20 ml of cell culture media and incubated at 37° C. in humidified 5% $CO_2$. Experiments were performed in duplicate or triplicate.

Cell Treatment and Assessment of Viability: Cells were plated in 96-well plates at a density of 60 cells/mm$^2$ in 50 µL of media. Approximately 24 hours after plating, 50 µL of media containing either menadione, rotenone, or antimycin A, either with or without PB1 and PB2, was added to the cells to generate the final concentrations of 10 nM, 1 µM, or 100 µM. Control wells received media containing vehicle alone. Following 24 hours of treatment, media was aspirated from wells using a 25-gauge needle and cells stained with calcein-AM (10 µg/mL) and propidium iodide (1 µg/mL) (both Invitrogen, Carlsbad, Calif.) in PBS for 30 minutes. The staining solution was aspirated using a 25-gauge needle and replaced with PBS. Three randomly chosen fields per well were photographed on an Axiovert 135 microscope under epifluorescence with a Nikon D70s digital SLR camera (Nikon, Melville, N.Y.) at a resolution of 3008×2000 pixels and an exposure time of 1.6 seconds. Live (calcein-positive) and dead (propidium iodide-positive) cells were assessed using Image) software. Pictures were batch analyzed using a macro containing the following actions: subtract background, threshold, erode, erode, watershed, and analyze particles between the sizes of 1000 pixels and infinity. The fidelity of automated counts was periodically confirmed by comparison with manual counts. Each experiment was analyzed with respect to its own set of controls to account for variation in passage number of the RGC-5 cells and small differences between batches of cryopreserved RGC-5 cells.

Statistics: Viability was assessed as number of live cells/ $mm^2$, and compared to the untreated controls of each experiment. Means were compared using Student's unpaired t-test.

Results

Figure 3:
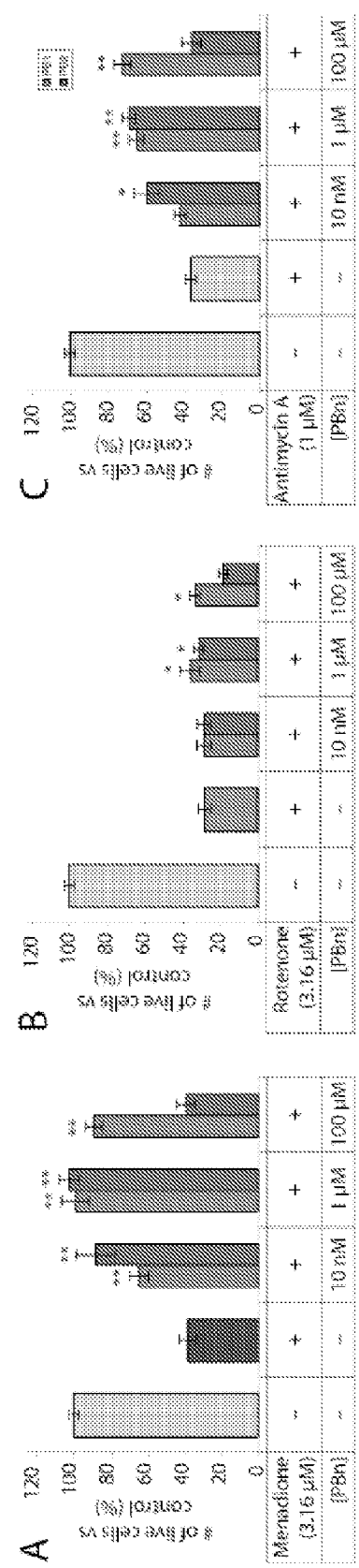
FIG. 3 A-C depict bar graphs of the number of live cells treated compared to control. PB1 (left bar of double bar) and PB2 (right bar of double bar) show significant protection against the mitochondrial toxins menadione (A) and antimycin A (C) (*–$p<0.05$, **–$p<0.01$) and the electron transport chain complex I inhibitor rotenone (B) (*–$p<0.05$). PB2 was toxic at 100 µM.
Figure 4A:
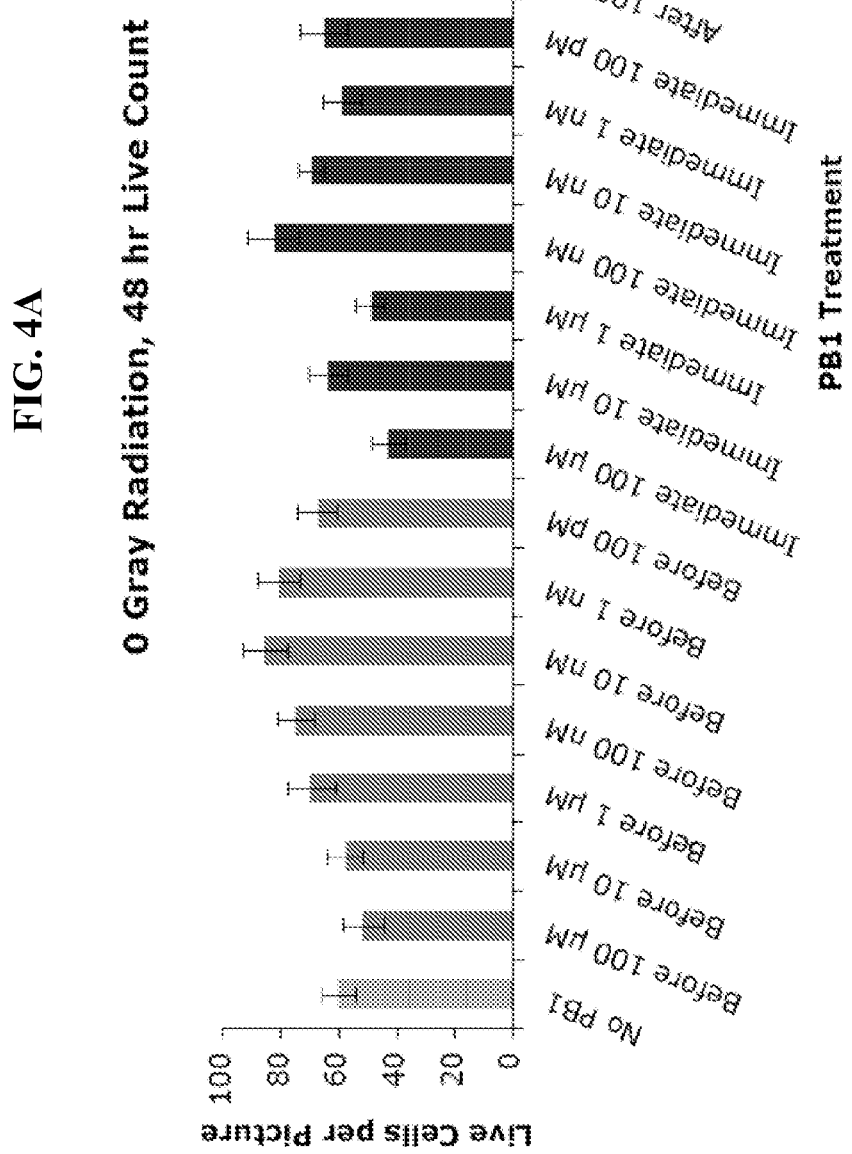
Figure 4B:
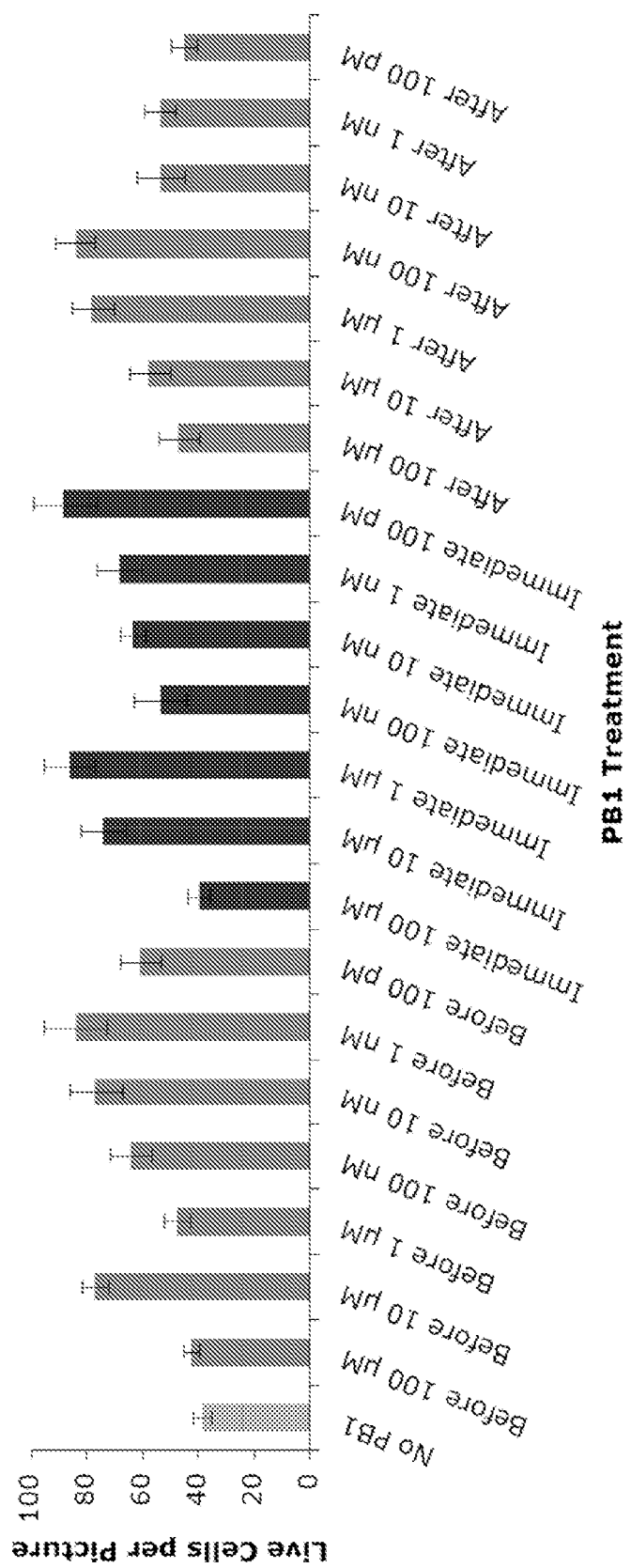
Figure 4C:
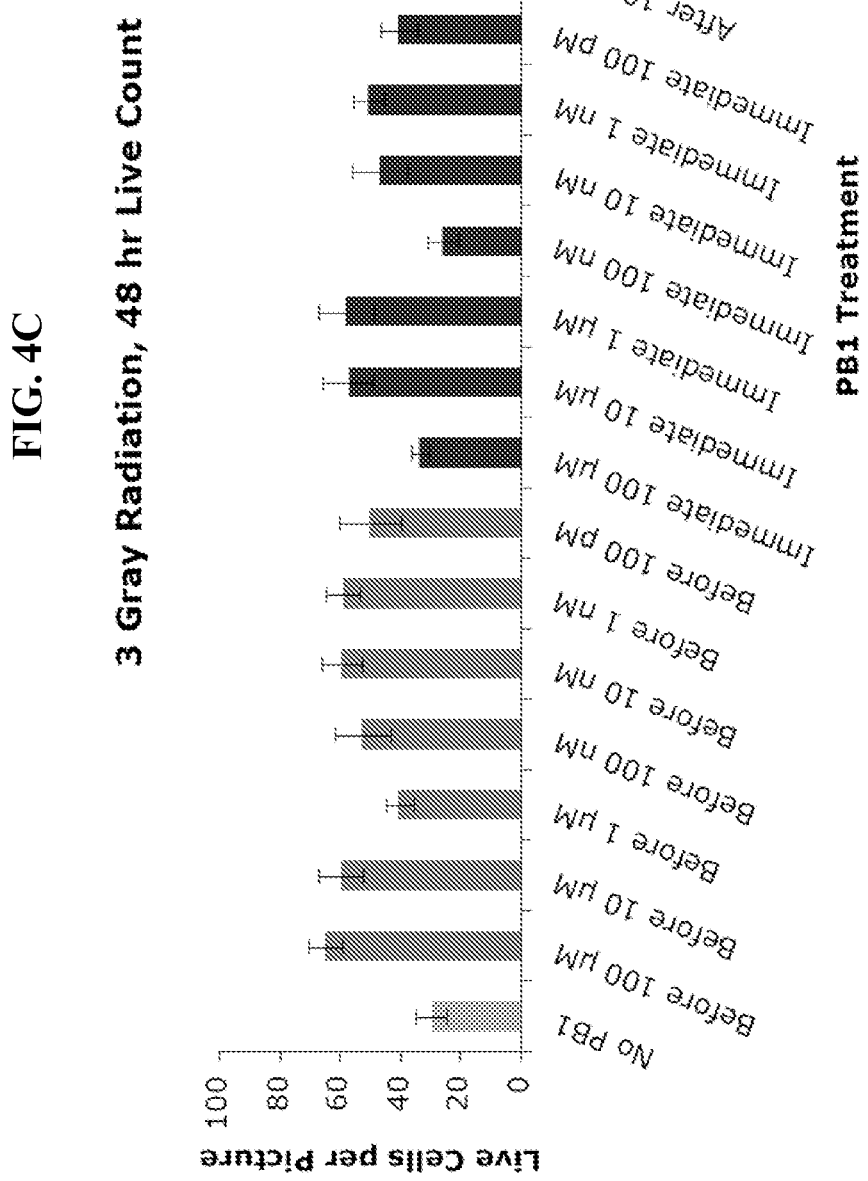
Figure 4D:
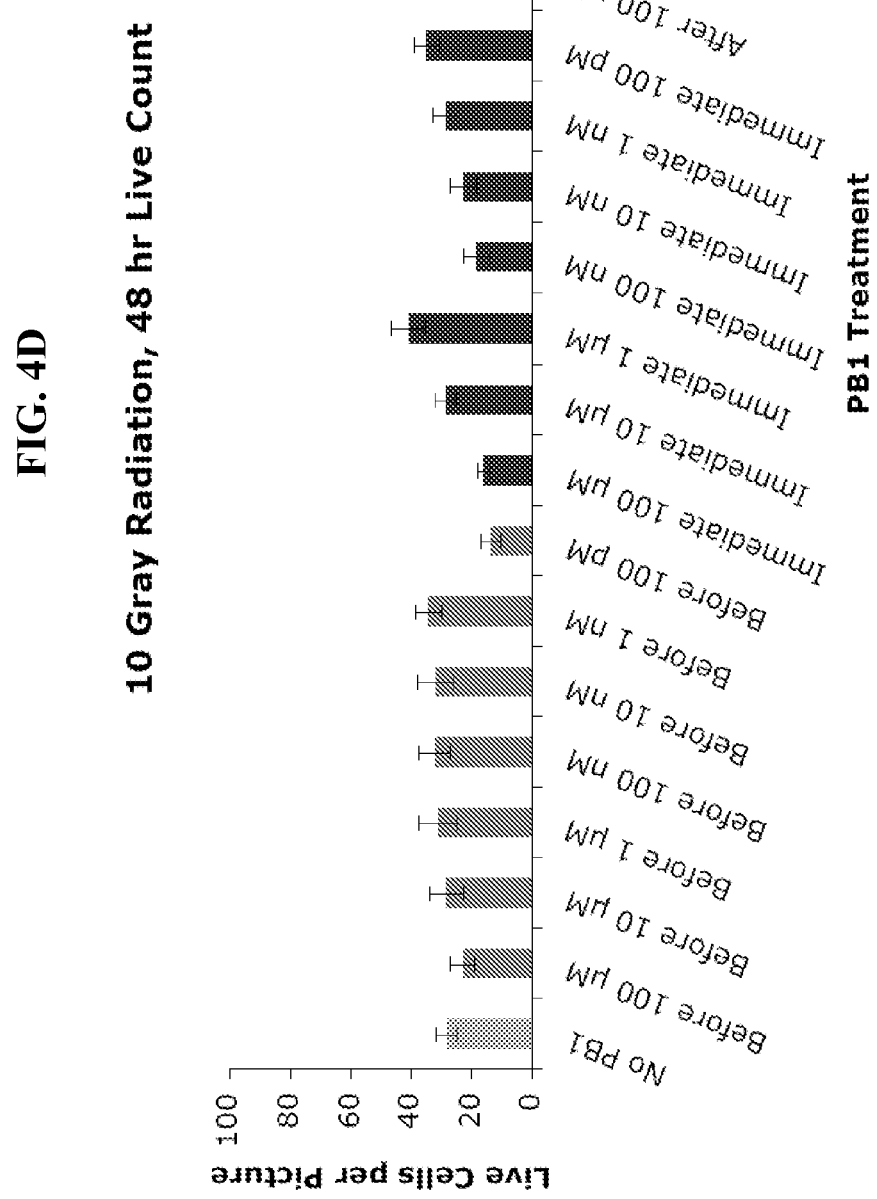
Figure 4E:
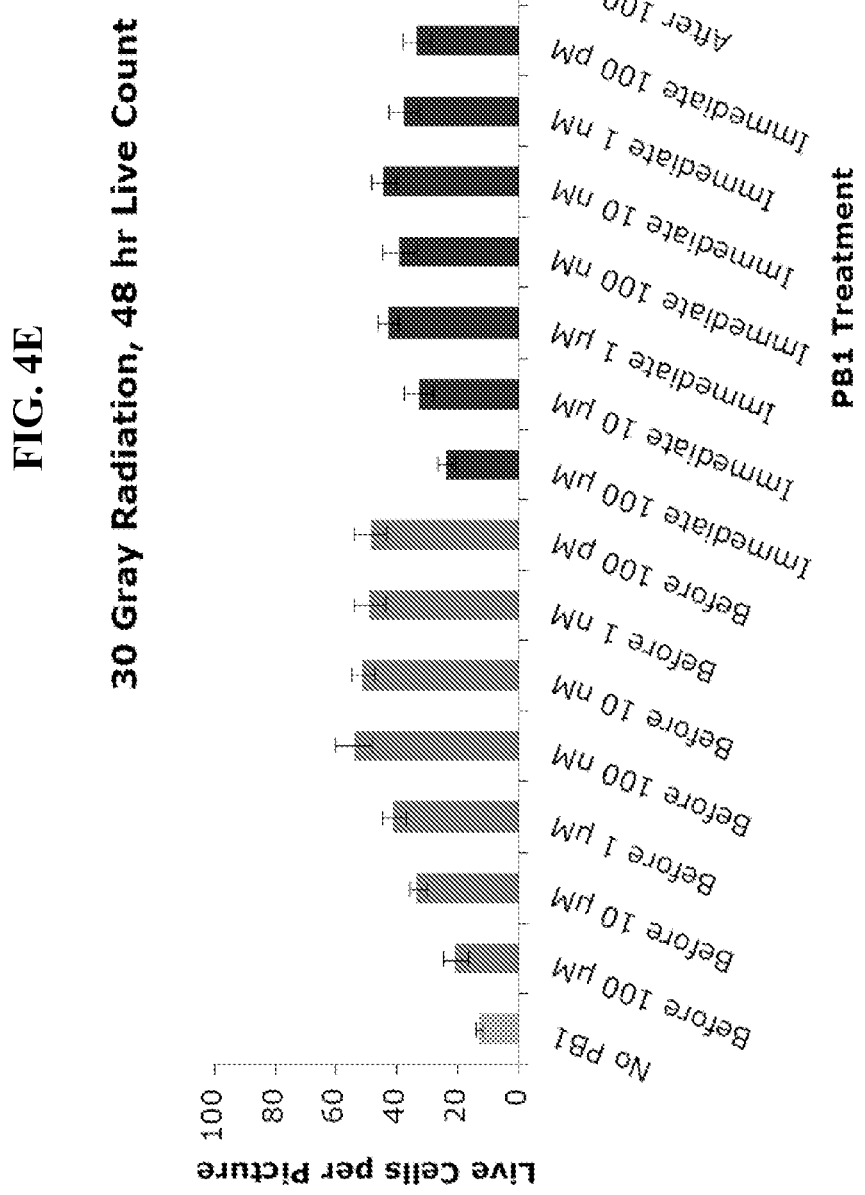
Figure 4F:
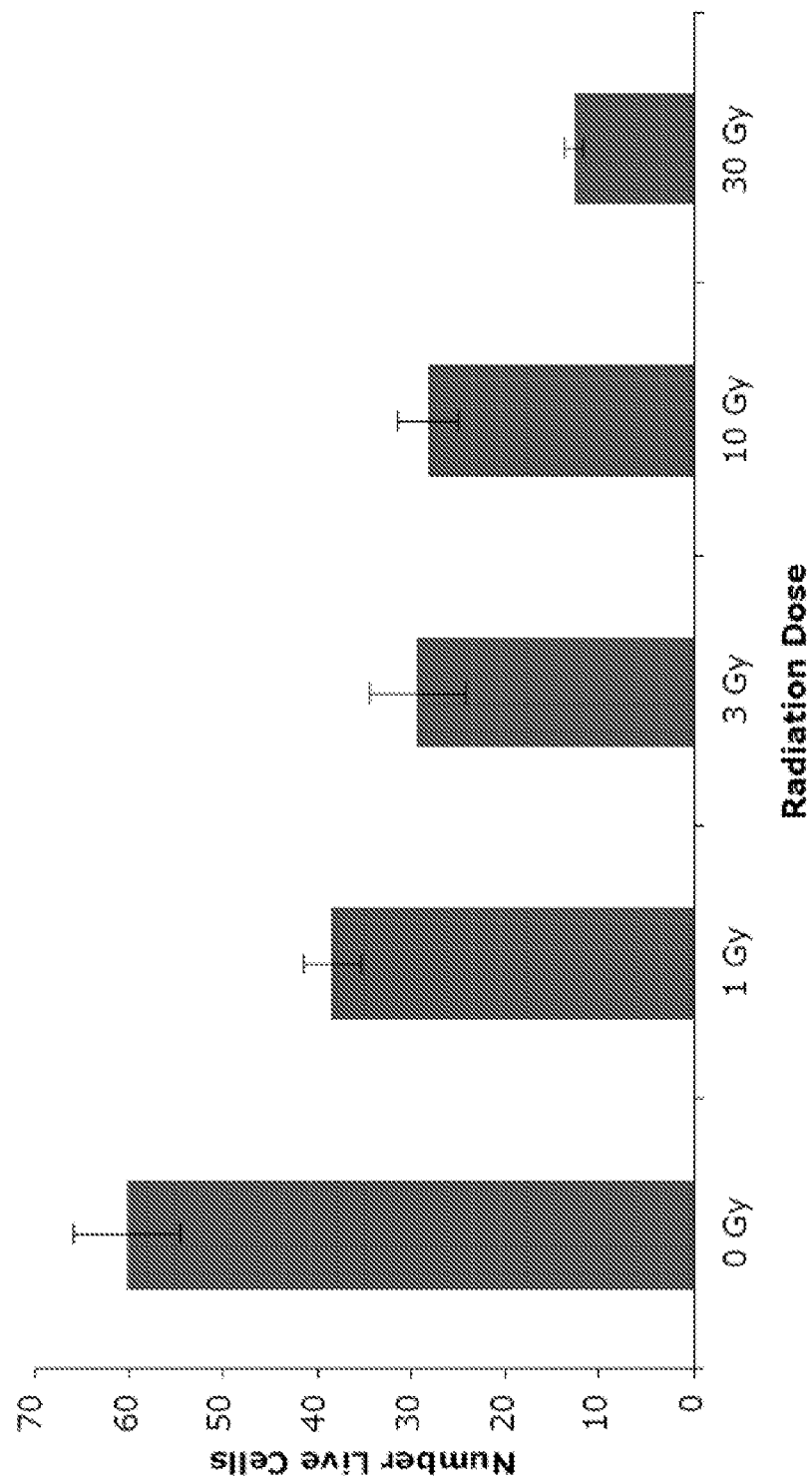
Figure 4G:
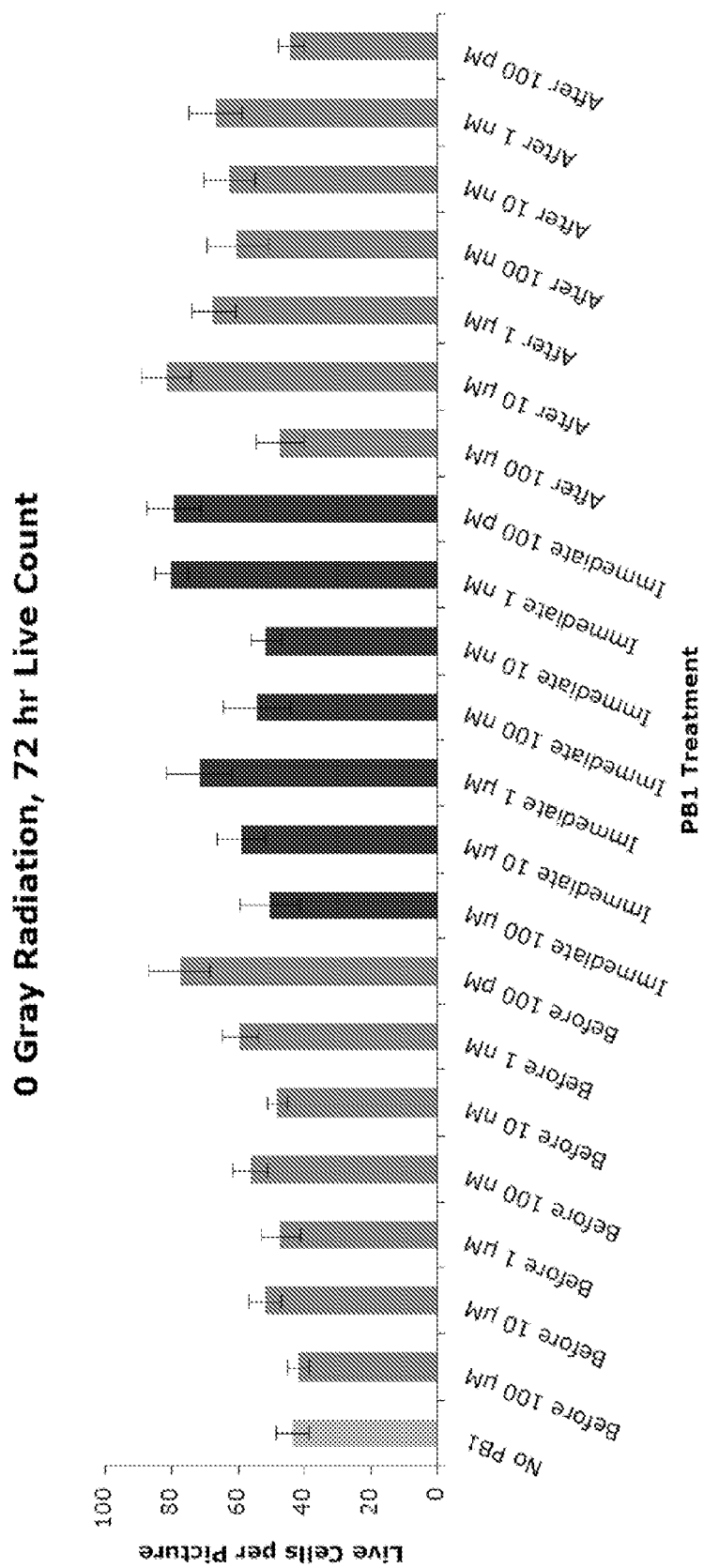
Figure 4I:
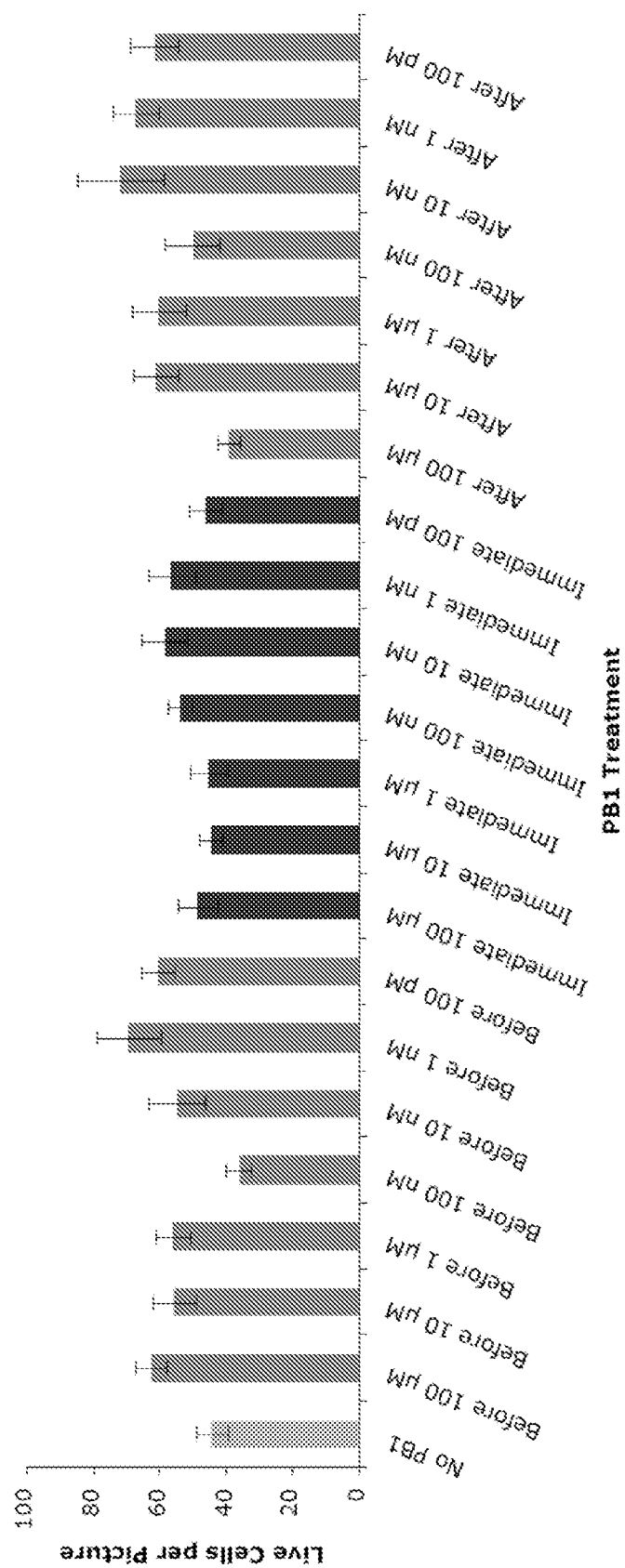
Figure 4J:
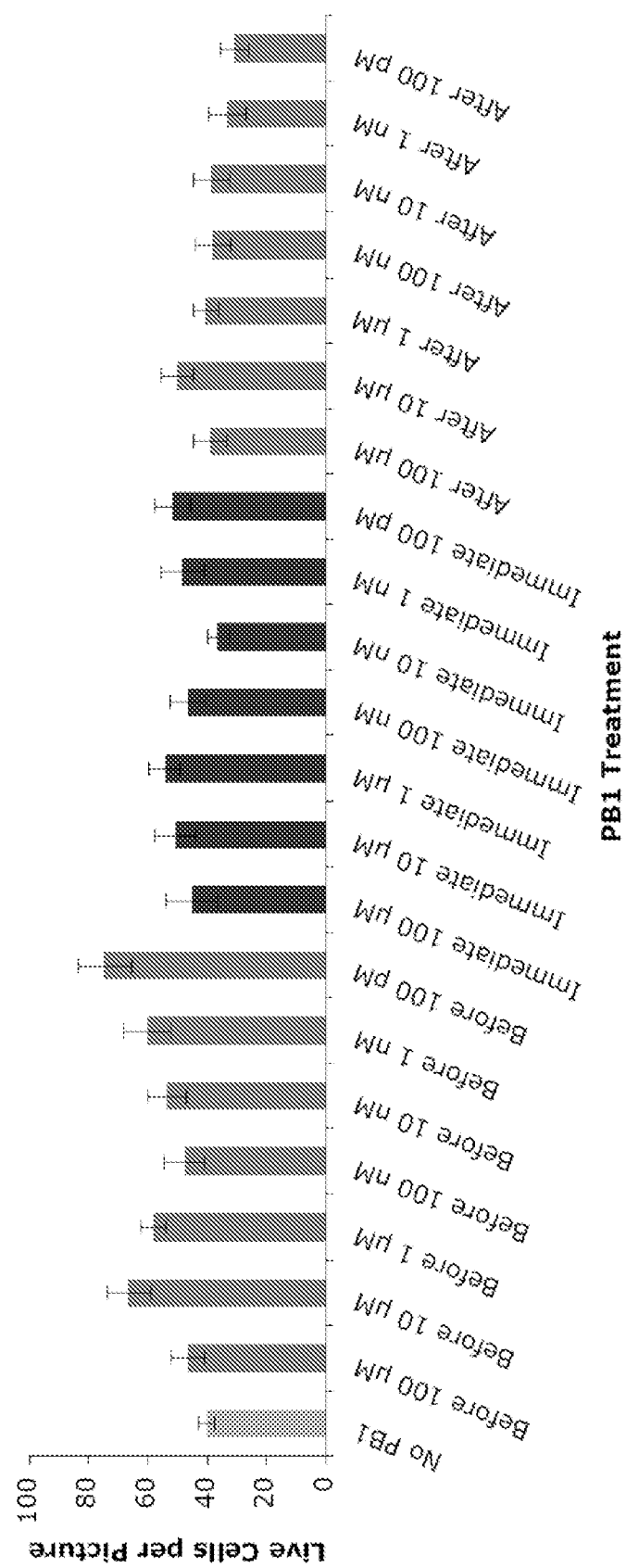
Figure 4K:
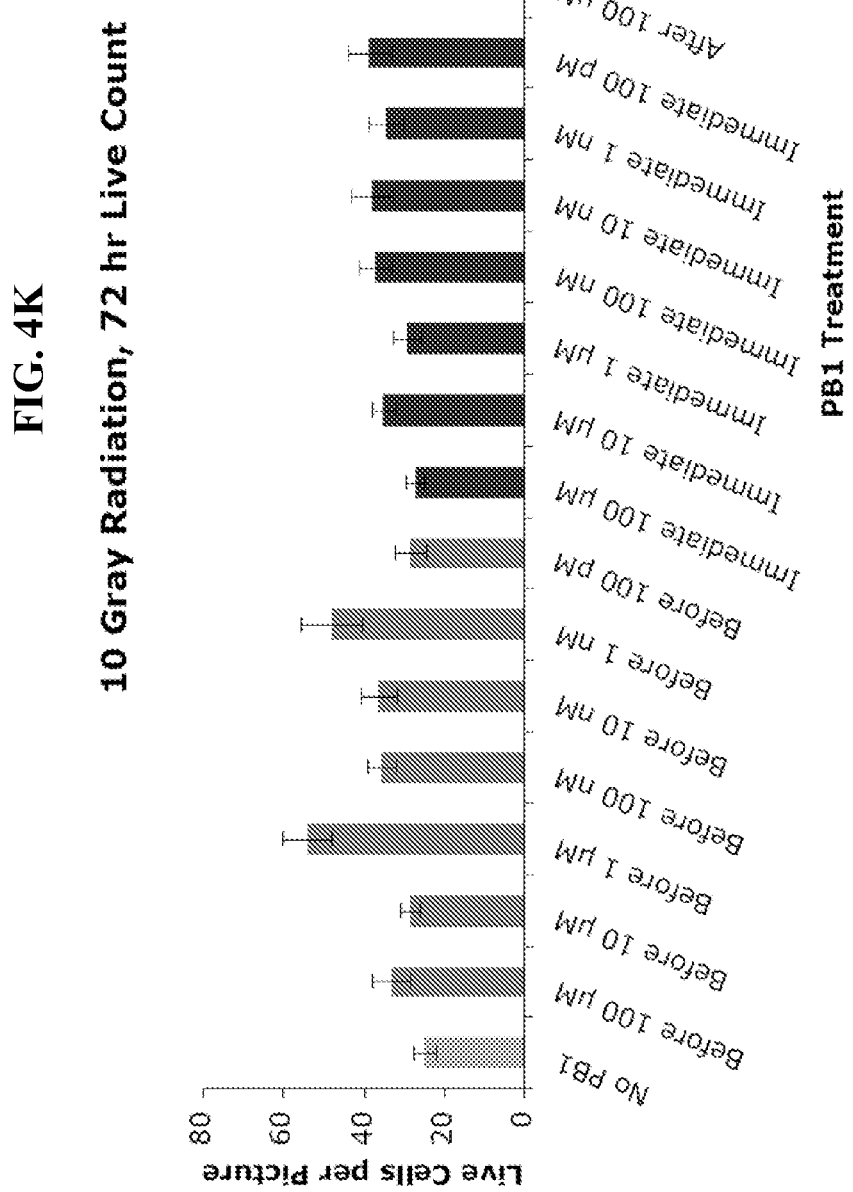
Figure 4L:
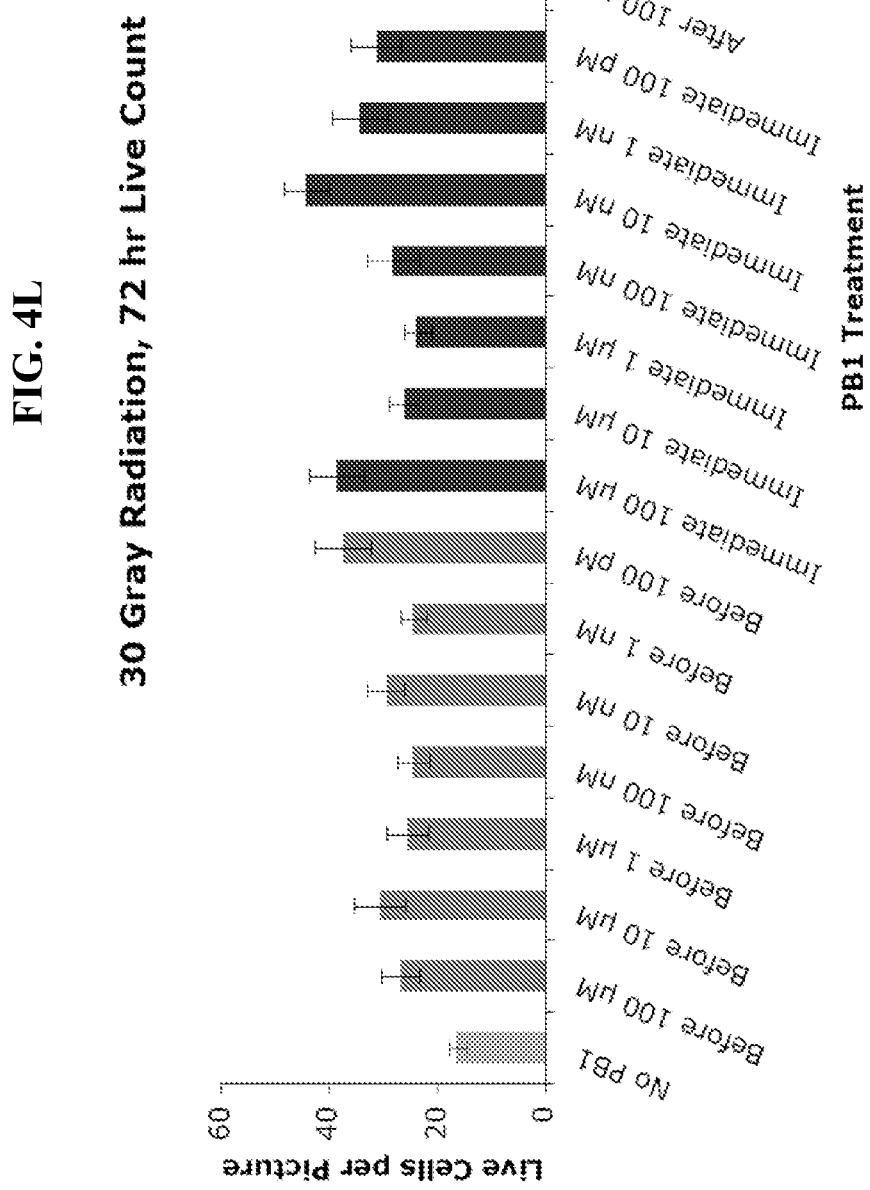

RGC-5 cells plated in 96-well plates were treated for 24 hours with the redox cycling agent menadione, the complex I inhibitor rotenone, or the complex III inhibitor antimycin A, at final concentrations ranging from 100 nM to 31.6 µM (menadione) or 1 µM to 316 µM (rotenone or antimycin A). Without additional treatment, menadione (3.16 µM), rotenone (3.16 µM), or antimycin A (1 µM) caused 50-70% cell death. RGC-5 cells were co-incubated with these mitochondrial electron transporter chain (METC)-drugs and the borane-phosphines PB1 or PB2 for 24 hours, followed by assessment of cell viability by calcein/propidium iodide assay. TCEP (100 µM) served as a positive control. PB1 and PB2 showed significant rescue of RGC-5 cells from death induced by the METC-active drugs menadione, rotenone, and antimycin A. PB1 was highly neuroprotective when given to RGC-5 cells at a final concentration of 100 µM against menadione (83±5% vs. 34±4%; p<0.0001) and against antimycin A (74±4% vs. 34±2%; p<0.0001). PB1 rescue from rotenone-induced oxidative stress was significant, but substantially less than for the other METC-active drugs (36±3% vs. 25±3%; p=0.01) (FIG. 3B). PB2 was highly neuroprotective at a final concentration of 1 µM against menadione (FIG. 3A; 95±5% vs. 34±4%; p<0.0001) and antimycin A (FIG. 3C; 68±3% vs. 34±2%; p<0.0001). Likewise, PB2 showed significant but substantially lower protection from rotenone (FIG. 3B; 34±2% vs. 25±3%; p=0.03). At higher concentrations, PB1 and PB2 showed little or no rescue of RGC-5 cells, most likely due to toxicity.

Example 3

Preventing Radiation-Induced Death of Retinal Endothelial Cells In Vitro

Experimental Procedures

The borane-protected phosphines bis(3-propionic acid methyl ester)phenylphosphine borane complex (PB1) and (3-propionic acid methyl ester)diphenylphosphine borane complex (PB2) were synthesized as described in Example 2.

Cell Culture: Murine endothelial cells were isolated from Immortomice, which express a temperature-sensitive Simian virus 40 large T antigen, using sheep anti-rat Dynabeads coated with the rat anti-mouse PECAM-1 monoclonal antibody MEC13.3. The cells were grown at 33° C. with 5% $CO_2$ on culture dishes coated with 1% gelatin, in DMEM with 20% FBS, 2 mM L-glutamine, 2 mM sodium pyrovate, 20 mM HEPES, 1% non-essential amino acids, 100 µg/mL streptomycin, 100 U/mL penicillin, heparin at 55 U/mL, endothelial growth supplement 100 µg/mL, and murine recombinant interferon-γ at 44 units/mL.

Irradiation and Viability Assays: The cells were plated onto 1% gelatin coated 96-well plates at a density of 2,000 cells per well. For irradiation, control and treatment groups were removed from the incubator. Treatment groups received single doses of radiation between 1 and 30 Gray using an irradiator containing $^{137}$Cesium (JL Shepherd & Associates) using a rotating platform to ensure uniform delivery. Control groups were left at room temperature during irradiation of the treatment groups. PB1 or PB2 was administered 18 hours before, immediately before, or 18 hours after irradiation. Media was aspirated 48 or 72 hours after irradiation using a 30 gauge needle and the cells were incubated in staining containing calcein-AM and propidium iodide in PBS for 30 minutes at room temperature in the dark. Digital photomicrographs of the wells were taken at a total magnification of 200× on a Zeiss Axiovert inverted microscope under epifluorescence. Calcein-positive (viable) and propidium iodide-positive (dead) cells were counted using NIH ImageJ software. Statistical significance was determined using the Student's t-tests.

Results

To assess the protective effects of PB1 and PB2 against exposure to ionizing radiation, 100 µM to 100 µM PB1 or PB2 were administered to cultured retinal endothelial cells 18 hours before, at the time of; or 18 hours after radiation. Survival of irradiated retinal endothelial cells was assessed 48 (FIG. 4A-F) or 72 (FIG. 4G-L) hours after irradiation. Both PB1 and PB2 were effective radio-protectants when administered before or at the time of irradiation. Viable cell counts assessed 72 hours after 3 Gy irradiation increased from 29±6% of non-irradiated control to 54±6% with 1 µM PB1 (p=0.005) when the compounds were administered at the time of irradiation. Treatment with 1 µM PB2 improved viability to 62±10% of control (p=0.01). This corresponds to 35% and 46% rescue for PB1 and PB2 respectively.

Figure 5:
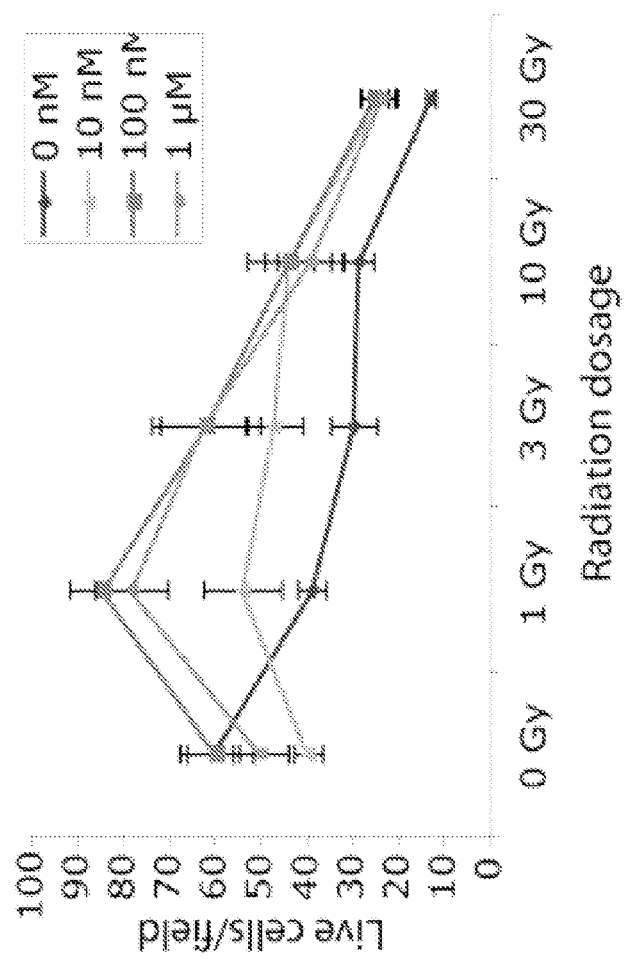
FIG. 5 shows PB1-mediated radiomitigation in retinal endothelial cells. Retinal endothelial cells were exposed to ionizing radiation up to 30 Gy. Addition of a range of PB1 doses 18 hours after exposure to ionizing radiation effected significant increases in viable cell counts (p-value was <0.05 for 100 nM and 1 µM at 1 Gy; for all doses shown at 3 Gy; for 100 nM at 10 Gy, and for all doses at 30 Gy).

Administration of PB1 18 hours after exposure to ionizing radiation up to 30 Gy also resulted in significant increases in viable cell counts (FIG. 5). Treatment with PB1 at 100 nM exhibited significant protection against all radiation exposures tested, and all PB1 treatment levels showed significant protection against 30 Gy radiation exposure (FIG. 5; p<0.05).

Example 4

Protection of Retinal Endothelial Cells from Oxidative Damage In Vitro

Experimental Procedures

The borane-protected phosphines bis(3-propionic acid methyl ester)phenylphosphine borane complex (PB1) and (3-propionic acid methyl ester)diphenylphosphine borane complex (PB2) were synthesized as described in Example 2.

Cell Culture: Murine endothelial cells were cultured as described in Experiment 3. Endothelial cells were treated directly with high levels of $H_2O_2$ in the absence or presence of PB1 and PB2 at a concentrations of 1-1000 µM. 1 µM was most effective against oxidative insults. Cell viability was assessed as described in Experiment 3 24 hours after administration of PB1 or PB2.

Superoxide scavenging: The ability of PB1 and PB2 to scavenge superoxide was quantified essentially as described (Schlieve et al., Invest. Opthalmol. Vis. Sci. 47:3878 (2006)). Essentially, fluorescence of hydroethidine was measured after exposure to superoxide generated by xanthine/xanthine oxidase, in the presence or absence of PB1, PB2, or polyethylene glycol-conjugated superoxide dismutase used as positive control.

Sulfhydryl reducing activity: Sulfhydryl reducing activity was measured with 5-5'-dithio-bis(2-nitrobenzoic acid) (DTNB), which undergoes a colorimetric change when its disulfide linkage is reduced. Reaction of various concentrations of dithiothreitol, tris(carboxyethyl)phosphine, PB1, or PB2 with 30 mM DTNB in methanol was carried out in buffer at pH 5, 7, and 9. The sulfhydryl reduction potentials of PB1 and PB2 were assessed both before and after borane deprotection with DABCO.

Results

PB1 and PB2 protected cultured retinal endothelial cells from oxidative damage, a known signaling pathway for various pathological conditions. PB1 and PB2 both exhibited a significant protective effect against $H_2O_2$ when administered at 1 µM levels, raising viable cell counts from 4.2±1.1% of control to 10.8±2.3% and 9.0±1.6%, respectively ($p<0.05$). This PB1 and PB2-mediated protection involves disulfide reduction, not superoxide scavenging. The borane-protected phosphines, thus, appear to interfere with the signaling of cell death after oxidative stress by inhibiting sulfhydryl oxidation.

We claim:

1. A compound selected from the group consisting of bis(3-propionic acid hexyl ester)phenylphosphine borane complex, (3-propionic acid hexyl ester)diphenylphosphine borane complex, bis(3-propyl pivalamide)phenylphosphine borane complex, (2-ethyl acetamide)diphenylphosphine borane complex, bis(3-propionic acid octyl ester)phenylphosphine borane complex, and bis(3-propionic acid decyl ester)phenylphosphine borane complex.

2. A pharmaceutical composition comprising:
a compound selected from the group consisting of bis(3-propionic acid hexyl ester)phenylphosphine borane complex, (3-propionic acid hexyl ester)diphenylphosphine borane complex, bis(3-propyl pivalamide)phenylphosphine borane complex, (2-ethyl acetamide)diphenylphosphine borane complex, bis(3-propionic acid octyl ester)phenylphosphine borane complex, and bis(3-propionic acid decyl ester)phenylphosphine borane complex; and
a pharmaceutically acceptable carrier.

3. A cell culture medium comprising:
a compound selected from the group consisting of bis(3-propionic acid hexyl ester)phenylphosphine borane complex, (3-propionic acid hexyl ester)diphenylphosphine borane complex, bis(3-propyl pivalamide)phenylphosphine borane complex, (2-ethyl acetamide)diphenylphosphine borane complex, bis(3-propionic acid octyl ester)phenylphosphine borane complex, and bis(3-propionic acid decyl ester)phenylphosphine borane complex.

4. A method for protecting a cell from cell death, the method comprising the step of:
exposing one or more cells to an effective amount of a compound selected from the group consisting of bis(3-propionic acid hexyl ester)phenylphosphine borane complex, (3-propionic acid hexyl ester)diphenylphosphine borane complex, bis(3-propyl pivalamide)phenylphosphine borane complex, (2-ethyl acetamide)diphenylphosphine borane complex, bis(3-propionic acid octyl ester)phenylphosphine borane complex, and bis(3-propionic acid decyl ester)phenylphosphine borane complex.

5. The method of claim 4, wherein the cells are human cells.

6. The method of claim 4, wherein the cells are neuronal cells.

7. The method of claim 4, wherein the cells are endothelial cells.

8. The method of claim 4, wherein the cells are protected in vivo in a human or in a non-human animal.

9. The method of claim 8, wherein protecting the cells in vivo treats a disease or a condition in a human or in a non-human animal.

10. The method of claim 9, wherein the disease or the condition is selected from the group consisting of a neurodegenerative disorder and a retinal ganglion cell death-related disease or condition.

11. A method for protecting a cell from effects of radiation, the method comprising the step of: exposing one or more neuronal cells to an effective amount of a compound selected from the group consisting of bis(3-propionic acid hexyl ester)phenylphosphine borane complex, (3-propionic acid hexyl ester)diphenylphosphine borane complex, bis(3-propyl pivalamide)phenylphosphine borane complex, (2-ethyl acetamide)diphenylphosphine borane complex, bis(3-propionic acid octyl ester)phenylphosphine borane complex, and bis(3-propionic acid decyl ester)phenylphosphine borane complex.

12. The method of claim 11, wherein the cell is protected in vivo in a human or in a non-human animal.

* * * * *